US012788928B2

(12) United States Patent
Wang

(10) Patent No.: US 12,788,928 B2
(45) Date of Patent: Nov. 10, 2026

(54) MOUTH-CLOSING DEVICE AND FIXING DEVICE FOR FIXING INTRAORAL APPARATUS

(71) Applicant: Lei Wang, Beijing (CN)

(72) Inventor: Lei Wang, Beijing (CN)

( * ) Notice: Subject to any disclaimer, the term of this patent is extended or adjusted under 35 U.S.C. 154(b) by 598 days.

(21) Appl. No.: 18/448,363

(22) Filed: Aug. 11, 2023

(65) Prior Publication Data

US 2023/0398321 A1 Dec. 14, 2023

Related U.S. Application Data

(63) Continuation-in-part of application No. PCT/CN2021/082511, filed on Mar. 24, 2021.

(51) Int. Cl.
*A61F 5/56* (2006.01)
*A61M 16/06* (2006.01)
(Continued)

(52) U.S. Cl.
CPC ......... *A61M 16/0688* (2014.02); *A61F 5/566* (2013.01); *A61C 7/08* (2013.01);
(Continued)

(58) Field of Classification Search
CPC ........... A61M 16/0688; A61M 16/0493; A61F 5/566; A61F 5/56; A61F 2005/563;
(Continued)

(56) References Cited

U.S. PATENT DOCUMENTS 3,203,417 A * 8/1965 Helmer ................ A63B 71/085 128/857
5,743,885 A * 4/1998 Hoerby ................. A61M 25/02 604/179
(Continued)

FOREIGN PATENT DOCUMENTS

CN 2693200 Y 4/2005
CN 102133141 A 7/2011
(Continued)

OTHER PUBLICATIONS

PCT International Search Report for PCT/CN2021/082511, dated Dec. 28, 2021.

*Primary Examiner* — Victoria Murphy
*Assistant Examiner* — Sara K Toich
(74) *Attorney, Agent, or Firm* — Flener IP & Business Law

(57) ABSTRACT

A mouth-closing device, comprising a mouth-closing patch (2), the mouth-closing patch (2) being fixed to a user's lips to maintain the user's mouth in a closed state; and further comprising one or more strip-shaped patches (7), the strip-shaped patch (7) being connected to the mouth-closing patch (2) and fixed to the user's face. A fixing device (1) is used for fixing an intraoral apparatus, the fixing device comprising the mouth-closing device, and further comprising a connecting mechanism, wherein the connecting mechanism is located between the mouth-closing patch (2) and the intraoral apparatus, and the mouth-closing patch (2) is connected to the intraoral apparatus by means of the connecting mechanism; the connecting mechanism comprises a connecting piece (3) and one or more fixing rings (4) connected to the connecting piece (3); and the connecting piece (3) is connected to the intraoral apparatus, the mouth-closing patch (2) passes through the fixing ring (4), and the mouth-closing patch (2) is fixed to the user's lips.

11 Claims, 7 Drawing Sheets

(51) Int. Cl.

| | |
|---|---|
| *A61C 7/08* | (2006.01) |
| *A61M 16/04* | (2006.01) |
| *A63B 71/08* | (2006.01) |

(52) U.S. Cl.
CPC .... *A61F 2005/563* (2013.01); *A61M 16/0493* (2014.02); *A63B 71/085* (2013.01)

(58) Field of Classification Search
CPC ......... A61C 70/08; A61C 7/08; A63B 71/085; A63B 2071/086–088
USPC .......................................................... 128/848
See application file for complete search history.

(56) References Cited

U.S. PATENT DOCUMENTS

| | | | | |
|---|---|---|---|---|
| 5,921,241 | A * | 7/1999 | Belfer | A61F 5/566 128/859 |
| 10,335,311 | B1 * | 7/2019 | Altman | A61F 5/566 |
| 2011/0180075 | A1 * | 7/2011 | Chen | A61M 16/0488 128/848 |
| 2013/0263861 | A1 * | 10/2013 | Holtzapple | A61M 16/0683 128/207.18 |
| 2020/0009342 | A1 * | 1/2020 | Drew | A61M 16/0688 |
| 2022/0313935 | A1 * | 10/2022 | Scott | A61M 16/047 |

FOREIGN PATENT DOCUMENTS

| | | | | |
|---|---|---|---|---|
| CN | 106422063 | A | 2/2017 | |
| JP | 2018051086 | A | 4/2018 | |
| TW | 201427722 | A | 7/2014 | |
| WO | WO-2014138506 | A1 * | 9/2014 | A61M 16/0688 |
| WO | 2019084482 | A1 | 5/2019 | |

* cited by examiner

MOUTH-CLOSING DEVICE AND FIXING DEVICE FOR FIXING INTRAORAL APPARATUS

CROSS-REFERENCE TO RELATED APPLICATIONS

This application is a continuation-in-part bypass of PCT/CN2021/082511, filed Mar. 24, 2021, the entire contents of which are incorporated herein by reference.

TECHNICAL FIELD

The present invention belongs to the field of fixing device technologies of medical equipment, and specifically to a mouth-closing device and a fixing device for fixing an intraoral apparatus.

BACKGROUND

Intraoral apparatuses are widely used to relieve conditions such as nocturnal teeth grinding, obstructive sleep apnea, and snoring. For example, trays and braces as intraoral apparatuses are used to isolate the contact between upper and lower teeth and to prevent the displacement of the upper and lower dentition along the occlusal surface to avoid dental damage due to grinding during sleep. Tongue retaining devices and mandibular advancement devices as intraoral apparatuses are used to control the position of the tongue during sleep to keep the tongue from collapsing toward the back of the mouth and obstructing the upper airway, leading to obstructive sleep apnea and snoring.

Since a user is unconscious during sleep, the ability to fix the intraoral apparatus reliably is a matter of efficacy and safety for the user. Most patients with nocturnal teeth grinding, obstructive sleep apnea, and snoring have the habit of sleeping on their backs and breathing through their mouths, which can easily cause the intraoral apparatus to fall out of position and pose the risk of aspiration and swallowing. Existing fixing devices for intraoral apparatuses can be categorized into the following four types.

The first type is to increase the size of the intraoral apparatus simultaneously by jamming the dentition through a baffle, making it difficult to disengage from its original position, or even if the apparatus is disengaged, the apparatus cannot be inhaled and swallowed. However, this type of fixing device has the following limitations: First, the apparatus is large in size and tends to cause discomfort. Second, a fixing mechanism is not tightly joined to the teeth and is prone to displacement. Third, the risk of fixation failure is increased in the case of mouth breathing.

In the second type, the intraoral apparatus is tightly clamped to the teeth by its own shape or by a device such as a clasp. However, this type of fixing device has the following limitations: First, the reliability of fixation is insufficient because the tooth surface is hard and smooth. Second, the intraoral apparatus may cause discomfort due to the tightness of clamping on the teeth. Third, the process is tedious if custom shaping is done for different tooth structures. If custom shaping is not done, the intraoral apparatus may suffer from mismatch, lack universality, and tend to fall off.

The third type is to implement fixation by connecting a barrier located outside the mouth or between the lips and teeth. However, this type of fixing device has the following limitations: First, although the barrier locks the intraoral apparatus in the direction of entering and leaving the oral cavity, the intraoral apparatus cannot be kept from lateral or rotational displacement. Second, the risk of fixation failure is increased in the case of mouth breathing. Third, the large size of the barrier tends to cause discomfort during wearing.

In a fourth type, the intraoral apparatus is connected to a rope or strap outside the mouth and is fixed to the head and neck, ear or clothing. However, this type of fixing device has the following limitations: First, the fixing position is far from the mouth, the rope or strap is long and flexible, the tolerance of fixation is large, and it is impossible to keep the intraoral apparatus from lateral, vertical, and rotational displacement and displacement away from the mouth. Second, the risk of fixation failure is increased in the case of mouth breathing. Third, it is difficult for the rope or strap to be tightly engaged with a connection hole, and the tolerance of fixation is large.

In addition, mouth-closing patches are also used as standalone apparatuses in the field of avoiding mouth breathing during sleep. Mouth breathing during sleep refers to that a patient opens the mouth and breathes through the mouth during sleep. Mouth breathing during sleep may cause the tongue to lose the restraint by upper and lower jaws and collapse toward the back of the mouth, blocking the upper airway and causing snoring. Mouth breathing during sleep can also cause a variety of diseases such as dryness and inflammation of the mouth and throat, and weathering damage to the teeth. Mouth breathing during sleep may also affect the treatment of obstructive sleep apnea. For example, during nasal continuous positive airway pressure (CPAP) treatment, mouth breathing may lead to air leakage from the mouth and failure to maintain positive air pressure. Mouth-closing patches can help a user to maintain the mouth in a closed state during sleep, to avoid mouth breathing. However, existing mouth-closing patches have significant limitations in terms of reliability of fixation.

The lips described herein include the upper and lower lips and an adjacent region at a periphery of the upper and lower lips, and existing mouth-closing patches are fixed to the lips. The small area of the upper and lower lips, the smooth surface, and the inward concavity of a connection area of the lips all are not conducive to the fixation of a mouth-closing patch. In addition, the skin of the upper and lower lips is more fragile and high viscosity adhesives cannot be used. In addition, for a user who grows a beard in an adjacent region at a periphery of the upper and lower lips as well as a user with oily skin or makeup, a mouth-closing patch cannot be reliably fixed in the region. Therefore, existing mouth-closing patches are not reliable enough in terms of fixation, and there is a risk of falling and aspiration.

SUMMARY OF THE INVENTION

To resolve the foregoing defects in the prior art, the present invention provides a mouth-closing device, the mouth-closing device including a mouth-closing patch. The mouth-closing patch is fixed to a user's lips to maintain the user's mouth in a closed state.

The mouth-closing device further includes one or more strip-shaped patches, and the strip-shaped patch is connected to the mouth-closing patch and is fixed to the user's face.

As one of the improvements to the foregoing technical solution, the mouth-closing patch has a stacked multilayer structure, and includes a substrate, a bonding layer, and a covering film; and

- the bonding layer is disposed on the substrate, and is used for bonding the mouth-closing patch to the lips, and the covering film covers the bonding layer.

As one of the improvements to the foregoing technical solution, the mouth-closing patch includes an upper end, a middle portion, and a lower end;

the upper end and the lower end both have large widths, the middle portion has a small width, and the middle portion and a fixing ring are tightly engaged; and a bending line is disposed at an end of the substrate.

As one of the improvements to the foregoing technical solution, the mouth-closing patch is fixed at an adjacent region at a periphery of the user's upper and lower lips, and a bonding layer is not arranged or a bonding layer with a covering film is arranged at the middle portion covering the user's upper and lower lips.

As one of the improvements to the foregoing technical solution, the substrate of the mouth-closing patch has a double-layer structure, and includes a base layer and a reinforcing layer that are arranged in a stacked manner.

As one of the improvements to the foregoing technical solution, the strip-shaped patch includes a fixing end, a connecting strap, and a bonding end;

the connecting strap is located between the fixing end and the bonding end, and the three have an integral structure;

the fixing end is connected to a side surface or an outer surface of the mouth-closing patch; and the bonding end is fixed to the user's face.

As one of the improvements to the foregoing technical solution, the strip-shaped patches are arranged in pairs, and each pair of strip-shaped patches are connected to two sides or the outer surface of the mouth-closing patch in a bilaterally symmetrical manner;

the bonding ends of each pair of strip-shaped patches are respectively fixed to the user's two cheeks; and the connecting straps of the plurality of strip-shaped patches may be connected and fused, the bonding ends of the plurality of strip-shaped patches may be connected and fused, and the fixing ends of the plurality of strip-shaped patches may be connected and fused.

As one of the improvements to the foregoing technical solution, an average width of the bonding ends is larger than an average width of the connecting straps of the strip-shaped patches; and an average width of the fixing ends of the strip-shaped patch is larger than the average width of the connecting straps.

The present invention further provides a fixing device for fixing an intraoral apparatus, including: the mouth-closing device;

the fixing device further includes a connecting mechanism;

the connecting mechanism is located between the mouth-closing patch and an intraoral apparatus, and the mouth-closing patch is connected to the intraoral apparatus by the connecting mechanism;

the connecting mechanism includes a connecting piece and one or more fixing rings connected to the connecting piece; and the connecting piece is connected to the intraoral apparatus, the mouth-closing patch passes through the fixing ring, and the mouth-closing patch is fixed to the user's lips.

As one of the improvements to the foregoing technical solution, the covering film further includes an upper covering film and a lower covering film, and a boundary line between the two is located at a position of the fixing ring on the mouth-closing patch; and the upper covering film and the lower covering film both cover the bonding layer.

As one of the improvements to the foregoing technical solution, the connecting piece has a sheet structure, and includes an extraoral end and an intraoral end, and a pair of surfaces formed by the connecting piece joined to the user's upper and lower lips are the largest surfaces of the connecting piece.

As one of the improvements to the foregoing technical solution, the connecting piece includes a plurality of sub-connecting pieces that are connected end to end; and a sub-connecting piece located at one end of the connecting piece is connected to the fixing ring, and a sub-connecting piece located at the other end is connected to the intraoral apparatus; and adjustment members for adjusting an overall length of the connecting piece are arranged at connections between the plurality of sub-connecting pieces connected end to end.

As one of the improvements to the foregoing technical solution, the fixing ring has a strip-shaped structure, and is tightly engaged with the mouth-closing patch, and the fixing ring includes a fixing ring body and a strip-shaped hole; and the strip-shaped hole is provided in the fixing ring body.

As one of the improvements to the foregoing technical solution, a plurality of fixing rings are provided; and an intraoral end of the connecting piece is connected to the intraoral apparatus, an extraoral end of the connecting piece is connected to the plurality of fixing rings arranged at equal intervals in a direction of entering and leaving the oral cavity, a corresponding fixing ring is selected according to the user's wearing position and comfort, and the mouth-closing patch passes through the selected fixing ring and is fixed to the user's lips.

As one of the improvements to the foregoing technical solution, the fixing device further includes a reinforcing patch; and the reinforcing patch covers an outer side of the fixing ring in which the mouth-closing patch is located, is bonded to the outer surface of the mouth-closing patch, and holds the fixing ring together with the mouth-closing patch.

As one of the improvements to the foregoing technical solution, a bonding layer is not arranged or a bonding layer with a covering film is arranged at a central portion of the reinforcing patch covering the fixing ring, and bonding layers are arranged at an upper end and a lower end of the reinforcing patch.

As one of the improvements to the foregoing technical solution, a side surface or an outer surface of the reinforcing patch is connected to the strip-shaped patch.

Compared with the prior art, the beneficial effects of the present invention are as follows:

1. In the mouth-closing device of the present invention, the mouth-closing patch 2 and the strip-shaped patch 7 provide multi-point fixation to reliably fix the mouth-closing device, to avoid the risk of aspiration.
2. The fixing device in the present invention can fix the mouth-closing patch 2 on an outer side of a user's mouth without a tolerance, and the strip-shaped patch 7 is used for strengthening, so that the precision and reliability of fixation are greatly improved. In addition, the mouth-closing patch 2 further makes the user to maintain the mouth in a closed state during sleep, so that the risk that the intraoral apparatus falls out of position is significantly reduced.
3. When the mouth is in a closed state, the sheet structure of the connecting piece 3 can inhibit the intraoral apparatus from lateral rotation. In addition, the connecting piece 3 is short and has no deformation, causing no tolerance of fixation in the direction of entering and leaving the oral cavity.

4. The fixing ring 4 and the mouth-closing patch 2 are tightly engaged, so that tolerances of fixation are reduced in a plurality of dimensions.
5. In the fixing device in the present invention, the reinforcing patch 6 is further added to the outer surface of the mouth-closing patch 2, so that the strip-shaped fixing ring 4 can be kept from moving or falling off, to further improve the precision and reliability of the fixing device 1.

Figure 1:
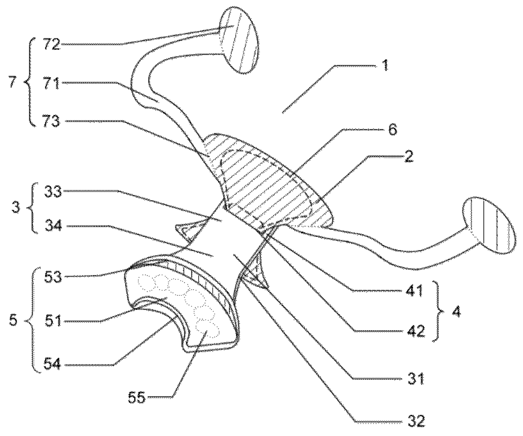
FIG. 1 is a schematic diagram of a structure of a fixing device that includes a mouth-closing device and is used for fixing an intraoral apparatus (tray) according to the present invention.

| Reference numerals: | |
|---|---|
| 1, | fixing device |
| 2, | mouth-closing patch |
| 3, | connecting piece |
| 4, | fixing ring |
| 5, | tray |
| 6, | reinforcing patch |
| 7, | strip-shaped patch |
| 8, | mandibular advancement device |
| 9, | tongue retaining device |
| 11, | upper and lower lips |
| 12, | adjacent region at a periphery of the upper and lower lips |
| 13, | front/outside direction of the oral cavity |
| 14, | rear/inside direction of the oral cavity |
| 15, | up direction of the oral cavity |
| 16, | down direction of the oral cavity |
| 21, | substrate |
| 22, | bonding layer |
| 23, | covering film |
| 24, | upper covering film |
| 25, | middle covering film |
| 26, | lower covering film |
| 27, | upper end |
| 28, | lower end |

-continued

| Reference numerals: | |
|---|---|
| 29, | middle portion |
| 211, | bending line |
| 212, | base layer |
| 213, | reinforcing layer |
| 31, | primary surface |
| 32, | secondary surface |
| 33, | extraoral end |
| 34, | intraoral end |
| 35, | hole |
| 36, | neck strap |
| 41, | fixing ring body |
| 42, | strip-shaped hole |
| 43, | first fixing ring |
| 44, | second fixing ring |
| 45, | third fixing ring |
| 51, | occlusal pad |
| 52, | connecting strap |
| 53, | external baffle |
| 54, | internal baffle |
| 55, | trench |
| 61, | central portion |
| 71, | connecting strap |
| 72, | bonding end |
| 73, | fixing end |
| 74, | first strip-shaped patch |
| 75, | second strip-shaped patch |
| 76, | third strip-shaped patch |
| 77, | fourth strip-shaped patch |

DETAILED DESCRIPTION

The present invention is further described with reference to the accompanying drawings.

The term "intraoral apparatus" in the present invention is correction or treatment equipment placed in the oral cavity, and includes, but not limited to, trays, braces, a mouthpiece, dental braces, a mandibular advancement device, and a tongue retaining device.

The term "connected" in the present invention refers to that two tangible objects are integrally connected together, or detachably connected together by a connecting member. A connection manner includes, but is not limited to, bonding, welding, insertion, a threaded connection, and a buckle connection.

Figure 5:
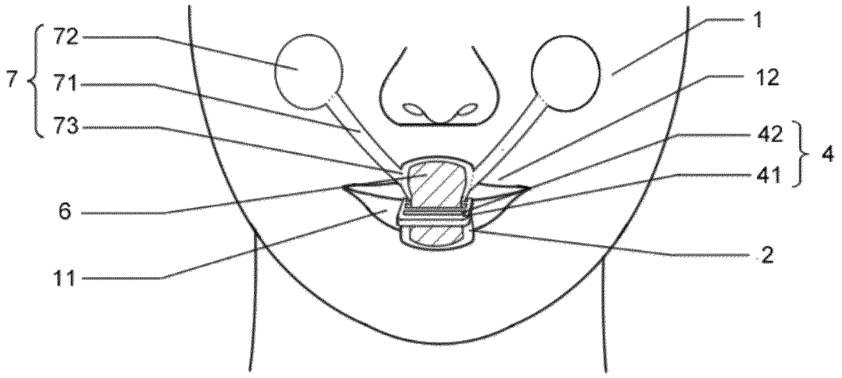
FIG. 5 is a schematic diagram of a structure of the fixing device for fixing the intraoral apparatus (tray) being installed on a user's lips according to the present invention in FIG. 1.

As shown in FIG. 5, the term "lips" in the present invention includes upper and lower lips 11 and an adjacent region 12 at a periphery of the upper and lower lips.

Figure 6:
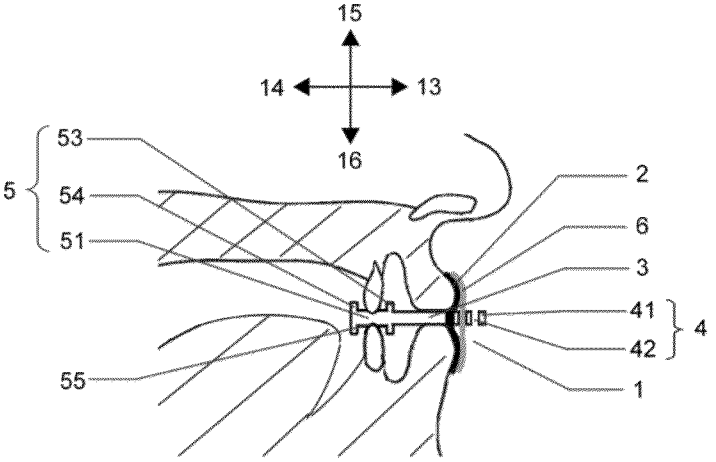
FIG. 6 is a side view of a structure of the fixing device for fixing the intraoral apparatus (tray) being installed on the user's lips according to the present invention in FIG. 5.

As shown in FIG. 6, directions of the oral cavity of the present invention are: a front/outside direction 13 of the oral cavity, a rear/inside direction 14 of the oral cavity, an up direction 15 of the oral cavity, and a down direction 16 of the oral cavity.

As shown in FIGS. 1 and 5, the present invention provides a fixing device for fixing an intraoral apparatus such as a tray, a mandibular advancement device, and a tongue retaining device. A fixing device 1 includes a mouth-closing device and a connecting mechanism.

The mouth-closing device includes a mouth-closing patch 2 and one or more strip-shaped patches 7.

The mouth-closing patch 2 is fixed to a user's lips to maintain the user's mouth in closed state. The strip-shaped patch 7 is connected to the mouth-closing patch 2 and is fixed to the user's face. The connecting mechanism is located between the mouth-closing patch 2 and an intraoral apparatus. The mouth-closing patch 2 is connected to the intraoral apparatus by the connecting mechanism.

The strip-shaped patch 7 is connected to a side surface or an outer surface of the mouth-closing patch 2 and is fixed to the user's face.

The connecting mechanism includes a connecting piece 3 and one or more fixing rings 4 connected to the connecting piece 3.

The connecting piece 3 is connected to the intraoral apparatus, the mouth-closing patch 2 passes through the fixing ring 4, and the mouth-closing patch 2 is fixed to the user's lips. Specifically, one end of the connecting piece 3 is connected to the fixing ring 4, and the other end of the connecting piece 3 is connected to the intraoral apparatus. The mouth-closing patch 2 collapsibly passes through the fixing ring 4 and is fixed to the user's lips.

Figure 2:
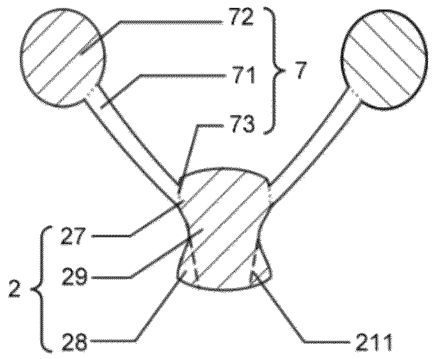
FIG. 2 is a schematic diagram of a structure of the mouth-closing device of the fixing device for fixing the intraoral apparatus (tray) according to the present invention in FIG. 1.

As shown in FIG. 1, FIG. 2, and FIG. 5, the mouth-closing patch 2 has a sheet structure, a pair of surfaces of the mouth-closing patch that are respectively joined to the lips and away from the lips are the largest surfaces of the mouth-closing patch.

Figure 4A:
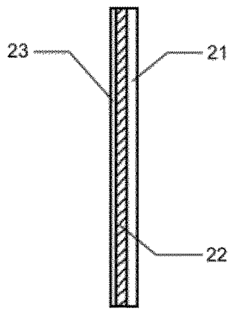
FIG. 4A is a side view of a mouth-closing patch of the fixing device for fixing the intraoral apparatus (tray) according to the present invention in FIG. 1, where a covering film is arranged on the mouth-closing patch.

As shown in FIG. 4A, the mouth-closing patch 2 has a stacked multilayer structure, and includes a substrate 21, a bonding layer 22, and a covering film 23. The bonding layer 22 is disposed on the substrate 21. The covering film 23 covers the bonding layer 22 for protecting the viscosity of the bonding layer 22. In a use process, after the covering film 23 is peeled off, the bonding layer 22 of the mouth-closing patch 2 is exposed and is bonded to the user's lips, to make the user maintain the mouth in a closed state.

Figure 4B:
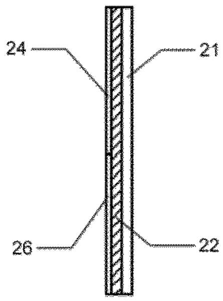
FIG. 4B is a side view of a mouth-closing patch of the fixing device for fixing the intraoral apparatus (tray) according to the present invention in FIG. 1, where an upper covering film and a lower covering film are arranged on the mouth-closing patch.
Figure 4C:
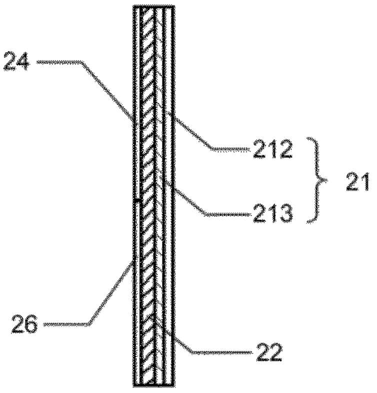
FIG. 4C is a side view of a mouth-closing patch of the fixing device for fixing the intraoral apparatus (tray) according to the present invention in FIG. 1, where a substrate of the mouth-closing patch includes a base layer and a reinforcing layer.

As shown in FIG. 4C, preferably, the substrate 21 has a double-layer structure, and includes a base layer 212 and a reinforcing layer 213 that are arranged in a stacked manner and are connected to each other. The high-strength or high-toughness reinforcing layer 213 is used to improve the strength or toughness of the mouth-closing patch 2, to avoid a tolerance of fixation caused by a flexible mouth-closing patch.

Figure 4D:
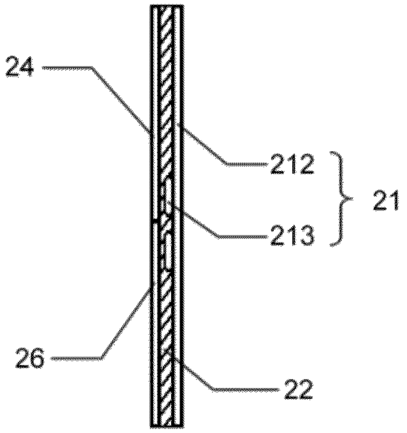
FIG. 4D is a side view of a mouth-closing patch of the fixing device for fixing the intraoral apparatus (tray) according to the present invention in FIG. 1, where a substrate of the mouth-closing patch includes a base layer and a reinforcing layer, and the reinforcing layer is two reinforcing strips.

As shown in FIG. 4D, preferably, the reinforcing layer 213 is two transversely arranged reinforcing strips fixed on the base layer 212. The reinforcing strip is located on an upper side and a lower side of the fixing ring 4, to improve the strength of a connection position between the mouth-closing patch 2 and the fixing ring 4.

As shown in FIG. 4B, preferably, the covering film 23 includes an upper covering film 24 and a lower covering film 26 that respectively cover an upper half portion and a lower half portion of the bonding layer 22 of the mouth-closing patch 2, and a boundary line between the two is located at a position of the fixing ring 4 surrounding the mouth-closing patch 2, so that the user can conveniently peel off the covering films after the fixing ring 4 is installed.

As shown in FIG. 2, the mouth-closing patch 2 includes an upper end 27, a lower end 28, and a middle portion 29.

The upper end 27 and the lower end 28 of the mouth-closing patch 2 are arranged to be wide, and the middle portion 29 is arranged to be narrow, to keep the fixing ring 4 from falling off from the mouth-closing patch 2. In addition, a bending line 211 is symmetrically disposed on the substrate of the upper end 27 or the lower end 28 of the mouth-closing patch 2. During assembly, the substrate on an outer side of the bending line 211 is bent toward an inner side, to narrow down the end of the mouth-closing patch 2, so that the end can completely and smoothly pass through the strip-shaped fixing ring 4, and make the fixing ring 4 tightly engaged with the middle portion 29 of the mouth-closing patch 2. Next, the bent part is unfolded, to keep the fixing ring 4 from falling off from the mouth-closing patch 2.

In another specific embodiment, to adapt to a user with sensitive skin on the upper and lower lips, the mouth-closing patch 2 is fixed at the adjacent region 12 at the periphery of the upper and lower lips, and a bonding layer is not arranged or a bonding layer with a covering film is arranged at the middle portion 29 covering the user's upper and lower lips, so that the middle portion 29 located between the user's upper and lower lips 11 is not bonded to the upper and lower lips 11, to keep the user's upper and lower lips from contact with an adhesive.

As shown in FIG. 1, FIG. 2, and FIG. 5, the strip-shaped patch 7 is used for increasing a quantity of fixing points and a fixing area of the mouth-closing device, to improve the reliability of fixation.

The strip-shaped patch 7 has a strip-shaped structure, and a pair of surfaces of the strip-shaped patch that are respectively close to the face and away from the face are the largest surfaces of the strip-shaped patch, and includes a fixing end 73, a connecting strap 71, and a bonding end 72. The connecting strap 71 is located between the fixing end 73 and the bonding end 72, and the three have an integral structure. The fixing end 73 of the strip-shaped patch 7 is connected to the side surface or the outer surface of the mouth-closing patch 2. The bonding end 72 of the strip-shaped patch 7 is fixed to the user's face. Preferably, the bonding end 72 is fixed to the user's cheekbone, which is particularly suitable for a user growing a beard.

Preferably, an average width of the bonding ends 72 is larger than an average width of the connecting straps 71 of the strip-shaped patches 7. The purpose of this is to increase a bonding area of the bonding end 72, to improve the reliability of bonding. Preferably, an average width of the fixing ends 73 of the strip-shaped patch 7 is larger than the average width of the connecting straps 71, to implement strengthening.

In another specific embodiment, the strip-shaped patches 7 appear in pairs. Each pair of strip-shaped patches 7 are bilaterally symmetrical. Each fixing end 73 of the strip-shaped patch 7 is connected to the mouth-closing patch 2, and the bonding end 72 of the strip-shaped patch is fixed to the user's two cheeks.

Figure 13:
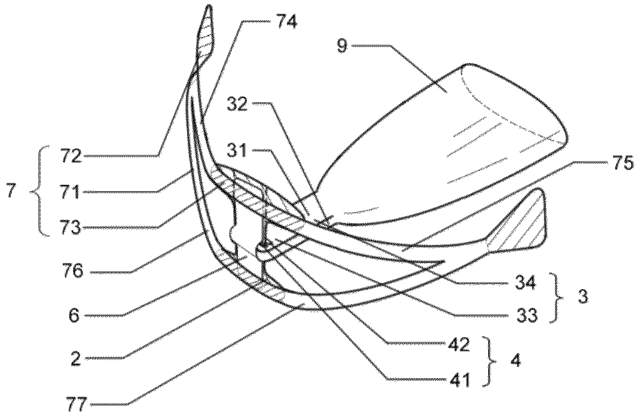
FIG. 13 is a schematic diagram of a structure of the fixing device for fixing the intraoral apparatus (tongue retaining device) according to the present invention.
Figure 14:
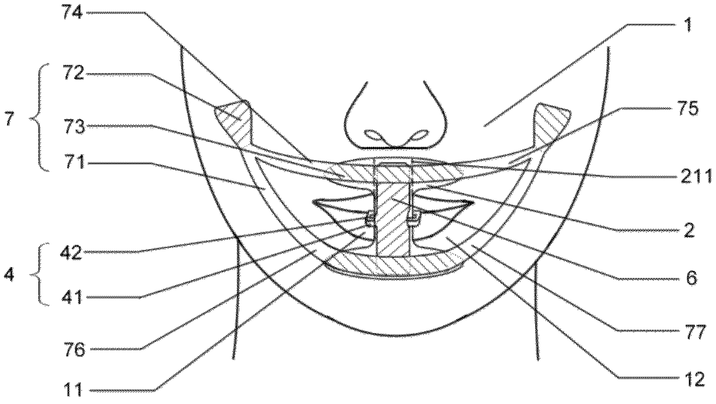
FIG. 14 is a schematic diagram of a structure of the fixing device for fixing the intraoral apparatus (tongue retaining device) being installed on a user's lips according to the present invention in FIG. 13.

As shown in FIGS. 13 and 14, the fixing ends 73 of the plurality of strip-shaped patches 7 may be connected and fused to each other, the connecting straps 71 of the plurality of strip-shaped patches 7 may be connected and fused to each other, and the bonding ends 72 of the plurality of strip-shaped patches 7 may be connected and fused to each other.

As shown in FIGS. 13 and 14, in another specific embodiment, after the fixing ring 4 is installed on the mouth-closing patch 2, the upper end 27 and the lower end 28 of the mouth-closing patch 2 are both connected to the strip-shaped patch 7, to keep the fixing ring 4 from falling off from the mouth-closing patch 2.

The bonding end 72 of the strip-shaped patch 7 is a multilayer structure, and includes a substrate, a bonding layer, and a covering film covering the surface of the bonding layer. Each of the connecting strap 71 and the fixing end 73 of the strip-shaped patch 7 includes a substrate, an optional bonding layer, and a covering film. A bonding layer and a covering film are usually not arranged on the connecting strap 71, to avoid bonding to a beard region. Preferably, the substrate of the strip-shaped patch 7 may have a double-layer structure, and includes a base layer and a reinforcing layer that are arranged in a stacked manner.

Figure 3A:
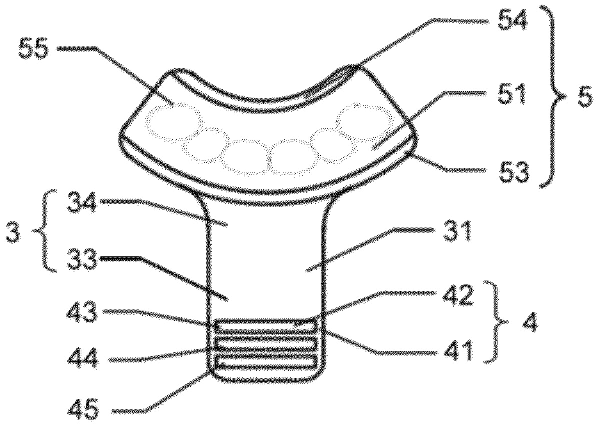
FIG. 3A is a schematic diagram of a structure of the tray of the fixing device for fixing the intraoral apparatus (tray) and a connecting mechanism according to the present invention in FIG. 1, where an occlusal pad is arranged on the tray.
Figure 3B:
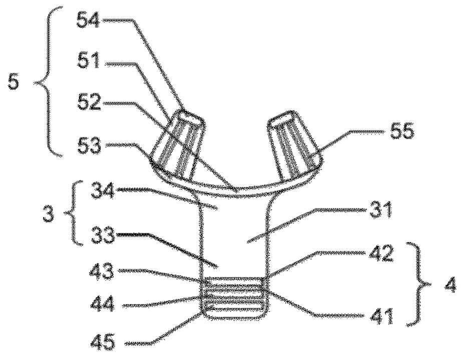
FIG. 3B is a schematic diagram of a structure of the tray of the fixing device for fixing the intraoral apparatus (tray) and a connecting mechanism according to the present invention in FIG. 1, where a connecting strap and two occlusal pads are arranged on the tray.

As shown in FIG. 1, FIG. 3A, and FIG. 3B, the connecting piece 3 includes an extraoral end 33 and an intraoral end 34. The intraoral end 34 is connected to the intraoral apparatus. The extraoral end 33 is connected to the fixing ring 4. The connection here is a detachable connection or an integral connection.

Preferably, the connecting piece 3 has a sheet structure. A pair of surfaces of the connecting piece joined to the upper and lower lips are primary surfaces 31 of the connecting piece 3, and the other surfaces are secondary surfaces 32. The primary surfaces 31 are the largest surfaces of the connecting piece 3. During wearing, the connecting piece 3 with the sheet structure is fixed by the lips and the upper and lower dentition, a tray 5 can be kept from rotational displacement. The primary surfaces 31 and the secondary surfaces 32 of the connecting piece 3 may be planar surfaces or curved surfaces. For example, in Embodiment 1, the primary surfaces 31 of the connecting piece 3 are planar surfaces, the secondary surfaces 32 are curved surfaces, and positions of the secondary surface 32 close to the tray 5 are bent toward two sides of the oral cavity, so that a position of a connection between the intraoral end 34 of the connecting piece 3 and the tray 5 is wider, to implement strengthening.

In another specific embodiment, to make the length of the connecting piece 3 adjustable, the connecting piece 3 includes a plurality of sub-connecting pieces that are connected end to end. A sub-connecting piece located at one end of the connecting piece 3 is connected to the fixing ring 4, and a sub-connecting piece located at the other end of the connecting piece 3 is connected to the intraoral apparatus. Adjustment members for adjusting an overall length of the connecting piece 3 are arranged at connections between the plurality of sub-connecting pieces connected end to end.

As shown in FIG. 1, FIG. 3A, and FIG. 3B, the fixing ring 4 has a strip-shaped structure, and includes a fixing ring body 41 and a strip-shaped hole 42. The strip-shaped hole 42 is provided in the fixing ring body 41. The fixing ring body 41 is connected to the connecting piece 3.

During wearing, the fixing ring 4 surrounds the mouth-closing patch 2, and is tightly engaged with the middle portion 29 of the mouth-closing patch 2, to reduce a tolerance of fixation. Preferably, a plurality of strip-shaped fixing rings are arranged on the connecting mechanism, and are arranged at equal intervals in a direction of entering and leaving the oral cavity. A corresponding fixing ring is selected according to the user's wearing position and comfort.

As shown in FIGS. 1 and 5, the fixing device 1 further includes a reinforcing patch 6. The reinforcing patch 6 has a sheet structure, and a pair of surfaces of the reinforcing patch that are respectively joined to the mouth-closing patch 2 and away from the mouth-closing patch 2 are the largest surfaces of the reinforcing patch. The reinforcing patch 6 covers an outer side of the fixing ring 4 in which the mouth-closing patch 2 is located, is bonded to the outer surface of the mouth-closing patch 2, and holds the fixing ring 4 together with the mouth-closing patch 2, to keep the fixing ring 4 from displacement or falling off.

The reinforcing patch 6 includes a substrate, a bonding layer, and a covering film covering a surface of the bonding layer. Preferably, the substrate has a double-layer structure, and includes a base layer and a reinforcing layer that are arranged in a stacked manner.

Figure 9:
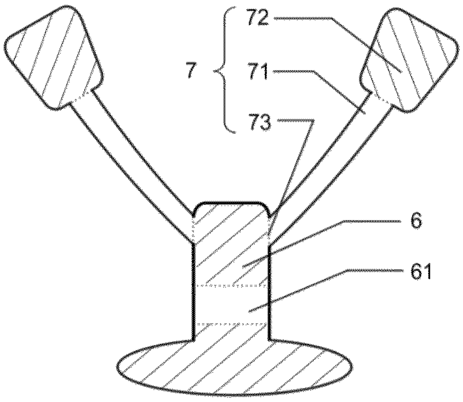
FIG. 9 is a schematic diagram of a structure of a reinforcing patch and a strip-shaped patch being connected of the fixing device for fixing the intraoral apparatus (mandibular advancement device) according to the present invention in FIG. 7.

As shown in FIG. 5 and FIG. 9, preferably, an upper end or/and a lower end of the reinforcing patch 6 is/are arranged to be wide, so that the reinforcing patch is bonded more firmly to the mouth-closing patch 2.

Figure 7:
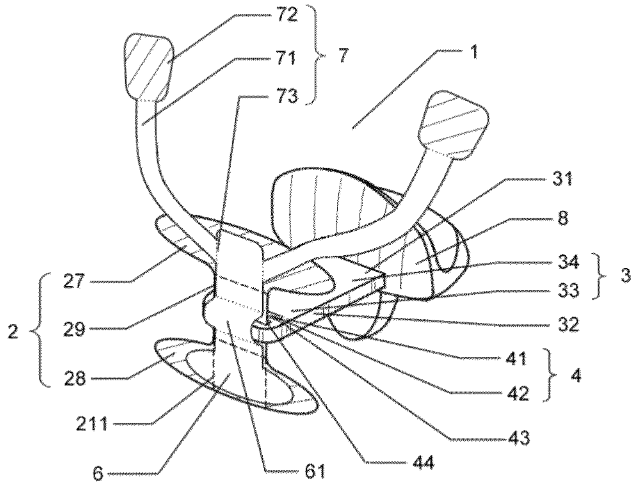
FIG. 7 is a schematic diagram of a structure of the fixing device for fixing the intraoral apparatus (mandibular advancement device) according to the present invention.
Figure 11:
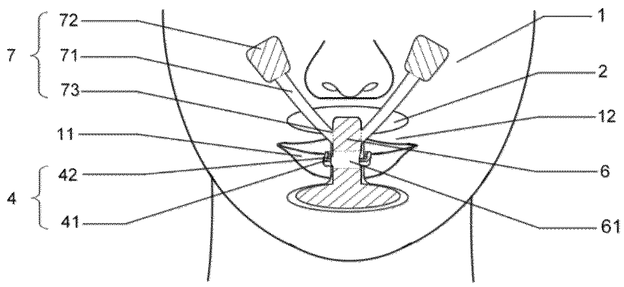
FIG. 11 is a schematic diagram of a structure of the fixing device for fixing the intraoral apparatus (mandibular advancement device) being installed on a user's lips according to the present invention in FIG. 7.

As shown in FIG. 7, FIG. 9, and FIG. 11, in another embodiment, a bonding layer is not arranged or a bonding layer with a covering film is arranged at a central portion 61 of the reinforcing patch 6 covering the fixing ring 4. In this case, the connecting mechanism may move slightly on the mouth-closing patch 2, to adapt to different wearing positions and angles. Bonding layers are arranged at the upper end and the lower end of the reinforcing patch 6, and are bonded to the outer surface of the mouth-closing patch 2, to fix the fixing ring 4.

As shown in FIGS. 13 and 14, in another specific embodiment, the strip-shaped patch 7 is connected to a side surface or an outer surface of the mouth-closing patch 2 or/and the reinforcing patch 6. After the reinforcing patch 6 is bonded to the mouth-closing patch 2, the two form a whole. Regardless of whether the strip-shaped patch 7 is connected to the reinforcing patch 6 or is connected to the mouth-closing patch 2, fixation can be implemented.

The fixing device 1 of the present invention can be fixed to the intraoral apparatus more safely and reliably, and mainly has the following characteristics:

1. The mouth-closing device maintains the oral cavity in a closed state, so that the risk that the intraoral apparatus falls out of position is generally reduced.
2. The structure of the mouth-closing patch 2, the connecting piece 3, the fixing ring 4, and the reinforcing patch 6 is used to fix the intraoral apparatus in a plurality of dimensions such as a longitudinal direction, a vertical direction, a transverse direction, and a rotational direction, to implement precise and reliable fixation.
3. The strip-shaped patch 7 enhances the reliability of fixation, to avoid the risk of aspiration and swallowing.
4. The main body of the fixing device 1 of the present invention is located outside the oral cavity, and does not stimulate the sensitive lining of the mouth.
5. To prevent the risk of aspiration and swallowing, existing intraoral apparatuses are usually large in size. The fixing device 1 of the present invention greatly improves the reliability of fixation, and the miniaturization in the development of the intraoral apparatus can be promoted.

Embodiment 1

FIG. 1, FIG. 2, FIG. 3A, FIG. 3B, FIG. 4A, FIG. 4B, FIG. 4C, FIG. 4D, FIG. 5, and FIG. 6 show a first embodiment of the present invention. The intraoral apparatus is the tray 5.

As shown in FIG. 1 and FIG. 5, the fixing device 1 for fixing a tray provided in the present invention includes a mouth-closing device and a connecting mechanism.

The mouth-closing device includes a mouth-closing patch 2 and two symmetrically arranged strip-shaped patches 7.

The mouth-closing patch 2 is fixed to a user's lips to maintain the user's mouth in a closed state.

Two strip-shaped patches 7 are integrally connected to two sides of the mouth-closing patch 2, and bonding ends 72 of the two strip-shaped patches 7 are respectively fixed to the user's two cheeks.

The connecting mechanism includes a connecting piece 3 and three fixing rings 4. The connecting mechanism is integrally fixed to the tray 5. The mouth-closing patch 2 collapsibly passes through the fixing ring 4 and is fixed to the user's lips.

As shown in FIG. 1 and FIG. 2, the mouth-closing patch 2 has a sheet structure, a pair of surfaces of the mouth-closing patch that are respectively close to the lips and away from the lips are the largest surfaces of the mouth-closing patch. The mouth-closing patch 2 includes an upper end 27, a lower end 28, and a middle portion 29. The upper end 27 and the lower end 28 of the mouth-closing patch 2 are arranged to be wide, and the middle portion 29 is arranged to be narrow, to keep the fixing ring 4 from falling off from the mouth-closing patch 2.

As shown in FIG. 4A, the mouth-closing patch 2 has a multilayer structure, and includes a substrate 21, a bonding layer 22, and a covering film 23. The bonding layer 22 is disposed on the substrate 21. The covering film 23 covers the bonding layer 22 for protecting the viscosity of the bonding layer 22. In a use process, after the covering film 23 is peeled off, the bonding layer 22 of the mouth-closing patch 2 is exposed and is bonded to the user's lips, to make the user maintain the mouth in a closed state.

As shown in FIG. 4C, preferably, the substrate 21 has a double-layer structure, and includes a base layer 212 and a reinforcing layer 213 that are arranged in a stacked manner and are connected to each other. The high-strength or high-toughness reinforcing layer 213 is used to improve the strength, toughness, or thickness of the mouth-closing patch 2, to avoid a tolerance of fixation caused by a flexible mouth-closing patch.

As shown in FIG. 4D, preferably, the reinforcing layer 213 is two transversely arranged reinforcing strips fixed on the base layer 212. The reinforcing strip is located on an upper side and a lower side of the fixing ring 4, to improve the strength of a connection position between the mouth-closing patch 2 and the fixing ring 4.

As shown in FIG. 4B, preferably, the covering film 23 includes an upper covering film 24 and a lower covering film 26 that respectively cover an upper half portion and a lower half portion of the bonding layer 22, and a boundary line between the two is located at a position of the fixing ring 4 surrounding the mouth-closing patch 2, so that the user can conveniently peel off the upper covering film 24 and the lower covering film 26 from the upper side and the lower side of the fixing ring after the fixing ring 4 is installed.

A bending line 211 is symmetrically disposed on the lower end 28 of the mouth-closing patch 2. During assembly, the substrate on an outer side of the bending line 211 is bent toward an inner side, to narrow down the lower end 28, so that the lower end 28 can completely and smoothly pass through the first fixing ring 43, and make the first fixing ring 43 tightly engaged with the middle portion 29 of the mouth-closing patch 2. Next, the bent part of the lower end 28 is unfolded, to keep the first fixing ring 43 from falling off from the mouth-closing patch 2.

As shown in FIG. 1 and FIG. 2, the strip-shaped patch 7 is used for increasing a quantity of fixing points and a fixing area of the mouth-closing device, to improve the reliability of fixation. The strip-shaped patch 7 has a strip-shaped structure, and a pair of surfaces of the strip-shaped patch that are respectively close to the face and away from the face are the largest surfaces of the strip-shaped patch, and includes a fixing end 73, a connecting strap 71, and a bonding end 72.

The connecting strap 71 is located between the fixing end 73 and the bonding end 72, and the three have an integral structure. The fixing end 73 of the strip-shaped patch 7 is integrally connected to a side surface of the mouth-closing patch 2. The bonding ends 72 of two strip-shaped patches 7 are respectively fixed to the user's two cheeks. The bonding ends 72 of the strip-shaped patches 7 are elliptical, and have an average width larger than an average width of the connecting straps 71, to increase a bonding area and improve the reliability of fixation.

The bonding end 72 of the strip-shaped patch 7 is a multilayer structure, and includes a substrate, a bonding layer, and a covering film covering the surface of the bonding layer. Each of the connecting strap 71 and the fixing end 73 of the strip-shaped patch 7 includes only a substrate. A bonding layer is not arranged on the connecting strap and the fixing end, to avoid bonding to a beard region. Preferably, the substrate of the strip-shaped patch 7 has a double-layer structure, and includes a base layer and a reinforcing layer. The reinforcing layer is used to improve the strength or toughness of the strip-shaped patch 7.

As shown in FIG. 1, FIG. 3A, and FIG. 3B, the connecting piece 3 includes an extraoral end 33 and an intraoral end 34. The intraoral end 34 is integrally connected to the tray 5. The extraoral end 33 is integrally connected to the fixing ring 4. The connecting piece 3 has a sheet structure. A pair of surfaces of the connecting piece joined to the upper and lower lips are primary surfaces 31, and the other surfaces are secondary surfaces 32. The primary surfaces 31 are the largest surfaces of the connecting piece 3. During wearing, the connecting piece 3 with the sheet structure is fixed by the lips and the upper and lower dentition, the tray 5 can be kept from rotational displacement. The secondary surfaces 32 are curved surfaces, and positions of the secondary surfaces close to the tray 5 are bent toward two sides of the oral cavity, so that a position of a connection between the intraoral end 34 of the connecting piece 3 and the tray 5 is wider, to implement strengthening.

As shown in FIG. 1, FIG. 3A, FIG. 3B, and FIG. 5, each fixing ring 4 includes a fixing ring body 41 and a strip-shaped hole 42. The strip-shaped hole 42 is provided in the fixing ring body 41. The three strip-shaped fixing rings (the first fixing ring 43, the second fixing ring 44, and the third fixing ring 45) are arranged at equal intervals in a direction of entering and leaving the oral cavity. The user selects a corresponding fixing ring according to the position and comfort of wearing, and the mouth-closing patch 2 passes through the selected fixing ring and is fixed to the user's lips.

As shown in FIGS. 1 and 5, the fixing device 1 further includes a reinforcing patch 6. The reinforcing patch 6 has a sheet structure, and a pair of surfaces of the reinforcing patch that are respectively joined to the mouth-closing patch 2 and away from the mouth-closing patch 2 are the largest surfaces of the reinforcing patch. The reinforcing patch 6 collapsibly passes through the second fixing ring 44, covers an outer side of the first fixing ring 43 in which the mouth-closing patch 2 is located, is bonded to the outer surface of the mouth-closing patch 2, and holds the first fixing ring 43 together with the mouth-closing patch 2, to keep the first fixing ring 43 from displacement or falling off. An upper end and a lower end of the reinforcing patch 6 are wide, so that the reinforcing patch is fixed to the mouth-closing patch 2 more firmly.

The reinforcing patch 6 includes a substrate, a bonding layer, and a covering film covering a surface of the bonding layer. The substrate with an adhesive may have a double-layer structure, and includes a base layer and a reinforcing layer. The reinforcing layer is used to improve the strength or toughness of the reinforcing patch 6.

As shown in FIG. 1, FIG. 3A, FIG. 5, and FIG. 6, the tray 5 is a molar tray, and includes an occlusal pad 51, an external baffle 53, and an internal baffle 54. The occlusal pad 51 has a sheet structure, and is used for making the upper and lower dentition maintain a spacing. A pair of primary surfaces of the occlusal pad that are in contact with the upper and lower dentition are the largest surfaces of the occlusal pad. Trenches 55 are provided in the primary surfaces of the occlusal pad 51 to avoid displacement of the upper and lower dentition along the occlusal surface of the teeth. Benefiting from the reliability of the fixing device 1 of the present invention, the occlusal pad 51 uses a lightweight and small-sized design, and is only located between the upper and lower incisors and canines.

Optionally, the external baffle 53 and the internal baffle 54 are perpendicular to the occlusal pad 51 and are respectively connected to an outer side and an inner side of the occlusal pad 51. The external baffle 53 and the internal baffle 54 are higher than the primary surfaces of the occlusal pad 51 in the upper position or/and the lower position and are clamped on two sides of the dentition to fix the tray 5. The external baffle 53 and the internal baffle 54 have different heights in the dentition direction, with a central portion being high and two sides being low, to improve the comfort. In another specific embodiment, another variant manner may be set for the heights of the external baffle 53 and the internal baffle 54 in the dentition direction.

In another specific embodiment, a plurality of occlusal pads 51 may be arranged on the tray 5. The sheet structures of the plurality of occlusal pads 51 are connected by one or more connecting straps 52. The connecting strap 52 has a strap-shaped structure, and may be connected to front portions or rear portions of the plurality of occlusal pads 51, or may be connected to the internal baffle 54 or the external baffle 53, to make the tray 5 into a whole.

Preferably, the connecting strap 52 may have variant heights in the up and down directions of the oral cavity and a bent shape, to assist in fixing the tray 5. The tray 5 shown in FIG. 3B includes two occlusal pads 51 that are located between upper and lower canines and are provided with trenches 55 in the surface. One internal baffle 54 and one external baffle 53 are respectively disposed on an inner side and an outer side of Each occlusal pad 51. The connecting strap 52 is connected to the external baffles 53 of the two occlusal pads 51. The connecting strap 52 has a high central portion and two low sides. Sides of the external baffle 53 and the internal baffle 54 close to connecting strap 52 are high, and sides of the baffles away from connecting strap 52 are low.

Preferably, the occlusal pad 51, the external baffle 53 or the internal baffle 54 has a double-layer structure, and includes an outer layer and an inner layer. The outer layer is used for shaping, and a soft material is chosen for the inner layer to improve comfort.

Preferably, a hole and a groove are provided in the occlusal pad 51, the external baffle 53 or the internal baffle 54 to implement a different function.

Preferably, the whole or the inner layer of the occlusal pad 51, the external baffle 53 or the internal baffle 54 is made of a thermoplastic material, in which the user may leave occlusal lines or tooth shapes through thermoplastic shaping, to achieve an optimal function.

Embodiment 2

FIG. 7, FIG. 8, FIG. 9, FIG. 10, FIG. 11, and FIG. 12 show a second preferred embodiment of the present invention. The intraoral apparatus is a mandibular advancement device 8.

As shown in FIG. 7 and FIG. 11, the fixing device 1 for fixing the mandibular advancement device 8 provided in the present invention includes a mouth-closing patch 2 and a connecting mechanism.

The connecting mechanism includes a connecting piece 3 and two fixing rings 4 connected to the connecting piece 3. The connecting mechanism is detachably fixed on the mandibular advancement device 8. The mouth-closing patch 2 collapsibly passes through the fixing rings 4 and is fixed at an adjacent region 12 at a periphery of a user's upper and lower lips.

Figure 8:
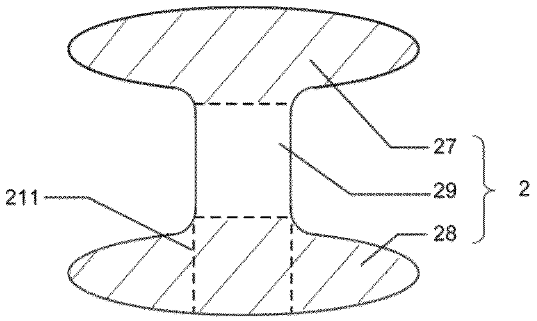
FIG. 8 is a schematic diagram of a structure of a mouth-closing patch of the fixing device for fixing the intraoral apparatus (mandibular advancement device) according to the present invention in FIG. 7.

As shown in FIG. 7 and FIG. 8, the mouth-closing patch 2 includes an upper end 27, a middle portion 29, and a lower end 28. The upper end 27 and the lower end 28 of the mouth-closing patch 2 are wide, and the middle portion 29 is narrow, to keep the fixing rings 4 from falling off.

A bending line 211 is symmetrically disposed on the lower end 28 of the mouth-closing patch 2. The substrate on an outer side of the bending line 211 is bent toward an inner side, to narrow down the lower end 28, so that the lower end 28 can completely and smoothly pass through the second fixing ring 44, and make the second fixing ring 44 tightly engaged with the middle portion 29 of the mouth-closing patch 2. Next, the bent part of the lower end 28 is unfolded, to keep the second fixing ring 44 from falling off from the mouth-closing patch 2.

Figure 10A:
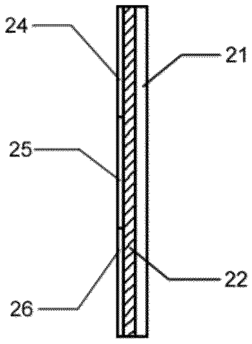
FIG. 10A is a side view of a mouth-closing patch of the fixing device for fixing the intraoral apparatus (mandibular advancement device) according to the present invention in FIG. 7, where an upper covering film, a middle covering film, and a lower covering film are arranged on the mouth-closing patch.

As shown in FIG. 10A, the mouth-closing patch 2 includes a substrate 21, a bonding layer 22, an upper covering film 24, a middle covering film 25, and a lower covering film 26.

The bonding layer 22 is disposed on the substrate 21, and the upper covering film 24, the middle covering film 25, and the lower covering film 26 are correspondingly arranged. In a use process, the upper covering film 24 and the lower covering film 26 are peeled off, and the exposed bonding layer 22 is fixed at the adjacent region 12 at the periphery of the upper and lower lips. The middle covering film 25 does not need to be peeled off, so that the mouth-closing patch 2 is not bonded to the user's upper and lower lips 11, to adapt to a user with skin on the lips sensitive to an adhesive.

Figure 10B:
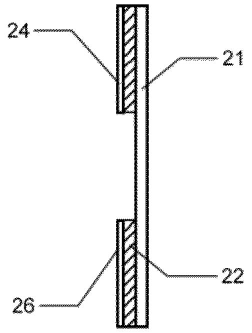
FIG. 10B is a side view of a mouth-closing patch of the fixing device for fixing the intraoral apparatus (mandibular advancement device) according to the present invention in FIG. 7, where a bonding layer is not arranged at a central portion of the mouth-closing patch.

In another specific embodiment, as shown in FIG. 10B, the mouth-closing patch 2 includes a substrate 21, a bonding layer 22, an upper covering film 24, and a lower covering film 26. The bonding layer 22 is disposed at an upper end and a lower end of the substrate 21, and the upper covering film 24 and the lower covering film 26 are correspondingly arranged. The bonding layer 22 is not arranged at a central portion of the substrate 21, so that the mouth-closing patch 2 is not bonded to the user's upper and lower lips 11, to adapt to a user with skin on the lips sensitive to an adhesive.

As shown in FIG. 7 and FIG. 11, the connecting mechanism includes a connecting piece 3 and one first fixing ring 43 and one second fixing ring 44 that are arranged in a direction of entering and leaving the oral cavity. The fixing rings 4 includes a fixing ring body 41 and a strip-shaped hole 42. The strip-shaped hole 42 is arranged in the fixing ring body 41.

The connecting piece 3 includes an extraoral end 33 and an intraoral end 34. The intraoral end 34 is detachably fixed on the mandibular advancement device 8. The extraoral end 33 is integrally connected to the first fixing ring 43 and the second fixing ring 44. The mouth-closing patch 2 passes through the second fixing ring 44 and is fixed to the adjacent region 12 at the periphery of the user's upper and lower lips.

As shown in FIG. 7, FIG. 9, and FIG. 11, the fixing device 1 further includes a reinforcing patch 6 and two strip-shaped patches 7 symmetrically connected to two sides of the reinforcing patch 6.

The reinforcing patch 6 has a sheet structure, and a pair of surfaces of the reinforcing patch that are respectively joined to the mouth-closing patch 2 and away from the mouth-closing patch 2 are the largest surfaces of the reinforcing patch. The reinforcing patch 6 covers an outer side of the second fixing ring 44 in which the mouth-closing patch 2 is located, is bonded to the outer surface of the mouth-closing patch 2, and holds the second fixing ring 44 together with the mouth-closing patch 2, to keep the second fixing ring 44 from displacement and falling off. An upper end and a lower end of the reinforcing patch 6 are respectively bonded to outer surfaces of the upper end 27 and the lower end 28 of the mouth-closing patch 2. A central portion 61 of the reinforcing patch 6 covers an outer side of the second fixing rings 44. A bonding layer is not arranged or a bonding layer with a covering film is arranged at the central portion 61 of the reinforcing patch, and is not bonded to the second fixing rings 44, to keep parts of the second fixing ring 44 being clamped by the mouth-closing patch 2 and the reinforcing patch 6 from being fixed by the bonding layer. In this case, the connecting mechanism may slightly move on the mouth-closing patch 2, to adapt to different wearing positions and angles. The lower end of the reinforcing patch 6 is wide, so that the reinforcing patch is more firmly fixed to the mouth-closing patch 2.

As shown in FIG. 7, FIG. 9, and FIG. 11, the strip-shaped patch 7 has a strip-shaped structure, and a pair of surfaces of the strip-shaped patch that are respectively close to the face and away from the face are the largest surfaces of the strip-shaped patch, and includes a fixing end 73, a connecting strap 71, and a bonding end 72. The connecting strap 71 is located between the fixing end 73 and the bonding end 72, and the three have an integral structure. The fixing end 73 of the strip-shaped patch 7 is integrally connected to a side surface of the reinforcing patch 6. The bonding end 72 of the strip-shaped patch 7 is trapezoidal, and has an average width larger than an average width of the connecting straps 71, to improve the reliability of bonding. Bonding ends 72 of two strip-shaped patches 7 are fixed to the user's two cheeks. No bonding layer is not arranged on the connecting straps 71 of the strip-shaped patches 7, to avoid bonding to a beard region.

Figure 12:
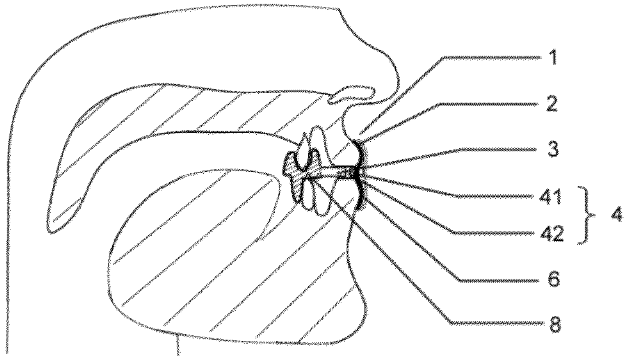
FIG. 12 is a side view of a structure of the fixing device for fixing the intraoral apparatus (mandibular advancement device) being installed on the user's lips according to the present invention in FIG. 11.

As shown in FIG. 7 and FIG. 12, the fixing device 1 of the present invention clamps the upper dentition through two tooth-shaped objects at an upper portion of the mandibular advancement device 8, and appropriate relative positions are maintained between a tooth-shaped object at a lower portion of the mandibular advancement device and the tooth-shaped objects at the upper portion. When the user closes the mouth, the tooth-shaped object at the lower portion pushes the lower dentition to the front of the oral cavity, and drives the mandible to move forward. In addition, the mouth-closing patch 2 is bonded to the user's lips, and the reinforcing patch 6 is bonded to an outer surface of the mouth-closing patch 2 to strengthen fixation, thereby keeping the fixing rings 4 from falling off.

Embodiment 3

Figure 15:
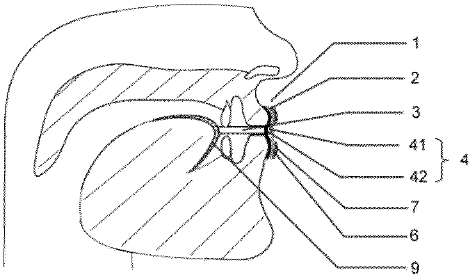
FIG. 15 is a side view of a structure of the fixing device for fixing the intraoral apparatus (tongue retaining device) being installed on the user's lips according to the present invention in FIG. 14.

FIG. 13, FIG. 14, and FIG. 15 show a third embodiment of the present invention. The intraoral apparatus is a tongue retaining device 9.

As shown in FIG. 13 and FIG. 14, the fixing device 1 for fixing the tongue retaining device 9 provided in the present invention includes a mouth-closing patch 2, a connecting mechanism, and two pairs of symmetrically arranged strip-shaped patches (four strip-shaped patches) 7.

The connecting mechanism is integrally fixed on the tongue retaining device 9. The mouth-closing patch 2 collapsibly passes through the connecting mechanism and is fixed to a user's lips.

As shown in FIG. 13 and FIG. 14, the mouth-closing patch 2 includes an upper end 27, a middle portion 29, and a lower end 28. The upper end 27 and the lower end 28 are wide, and the middle portion 29 is narrow.

A bending line 211 is symmetrically disposed on the upper end 27 of the mouth-closing patch 2. The substrate 21 on an outer side of the bending line 211 is bent toward an inner side, to narrow down the upper end 27, so that the upper end 27 can completely and smoothly pass through a fixing ring 4, and make the fixing ring 4 tightly engaged with the middle portion 29 of the mouth-closing patch 2. Next, the bent part of the upper end 27 is unfolded, to keep the fixing ring 4 from falling off from the mouth-closing patch 2.

The mouth-closing patch 2 is a multilayer structure. As shown in FIG. 4B, the mouth-closing patch 2 includes a substrate 21, a bonding layer 22, an upper covering film 24, and a lower covering film 26. The bonding layer 22 is disposed on the substrate 21. The upper covering film 24 and the lower covering film 26 cover the bonding layer 22 for protecting the viscosity of the bonding layer 22. In a use process, after the mouth-closing patch 2 enters the fixing ring 4, the upper covering film 24 and the lower covering film 26 can be conveniently peeled off to expose the bonding layer 22 of the mouth-closing patch 2 and bond the bonding layer to the user's lips, to make the user maintain the mouth in a closed state.

As shown in FIG. 13, the connecting mechanism includes a connecting piece 3 and a fixing ring 4. The connecting piece 3 includes an extraoral end 33 and an intraoral end 34. The intraoral end 34 is integrally connected to the tongue retaining device 9. The extraoral end 33 is integrally connected to the fixing ring 4. The mouth-closing patch 2 passes through the fixing ring 4 and is fixed to the user's lips.

The fixing ring 4 includes a fixing ring body 41 and a strip-shaped hole 42. The strip-shaped hole 42 is provided in the fixing ring body 41.

As shown in FIG. 13 and FIG. 14, the fixing device 1 further includes a reinforcing patch 6 and two pairs of symmetrically arranged strip-shaped patches 7. The reinforcing patch 6 covers an outer side of the strip-shaped fixing ring 4 in which the mouth-closing patch 2 is located, is bonded to the outer surface of the mouth-closing patch 2, and holds the fixing ring 4 together with the mouth-closing patch 2.

The two pairs of symmetrically arranged strip-shaped patches 7 are respectively a first strip-shaped patch 74, a second strip-shaped patch 75, a third strip-shaped patch 76, and a fourth strip-shaped patch 77, which are all connected to outer surfaces of the mouth-closing patch 2 and the reinforcing patch 6 in a bonding manner. The first strip-shaped patch 74 and the second strip-shaped patch 75 are connected to upper ends of the mouth-closing patch 2 and the reinforcing patch 6. The third strip-shaped patch 76 and the fourth strip-shaped patch 77 are connected to lower ends of the mouth-closing patch 2 and the reinforcing patch 6, so that the fixing rings 4 can be kept from falling off.

Each strip-shaped patch 7 includes a fixing end 73, a connecting strap 71, and a bonding end 72. The connecting strap 71 is located between the fixing end 73 and the bonding end 72, and the three have an integral structure. A bonding layer is disposed on the fixing end 73 of the strip-shaped patch 7, and is connected to the outer surfaces of the mouth-closing patch 2 and the reinforcing patch 6 in a bonding manner. A bonding layer is not arranged on the connecting strap 71, to avoid bonding to a beard region. The fixing ends 73 of the first strip-shaped patch 74 and the second strip-shaped patch 75 that are symmetrically arranged are integrally connected, and the fixing ends 73 of the third strip-shaped patch 76 and the fourth strip-shaped patch 77 are integrally connected, so that the structure is simpler and the connection is firmer. The bonding ends 72 of the first strip-shaped patch 74 and the third strip-shaped patch 76 located on the same side of the face are integrally connected and fused, and the bonding ends 72 of the second strip-shaped patch 75 and the fourth strip-shaped patch 77 are integrally connected and fused, so that a total quantity of the bonding ends 72 is reduced to 2. The two bonding ends 72 are both disposed on the bonding layer, and are respectively fixed to the user's two cheeks. The bonding ends 72 are triangular, and have an average width larger than an average width of the connecting straps 71, thereby improving the reliability of bonding. Preferably, an average width of the fixing ends 73 is larger than the average width of the connecting straps 71, to make a connection between the strip-shaped patch 7 and the mouth-closing patch 2 and the reinforcing patch 6 firmer.

As shown in FIG. 15, the tongue retaining device 9 is an elastic hollow cup-shaped object made of a plastic material. When the tongue enters the cup-shaped object, air in the cup-shaped object is pushed out. When the tongue moves toward the rear of the oral cavity, an air pressure difference is formed between the inside and outside of the cup-shaped object, to fix the tongue inside the cup-shaped object.

Embodiment 4

Figure 16:
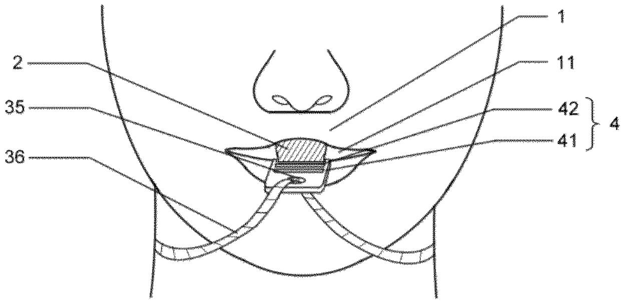
FIG. 16 is a schematic diagram of a structure of a fourth embodiment of a fixing device for fixing an intraoral apparatus being installed on a user's lips according to the present invention.

FIG. 16 shows a fourth embodiment of the present invention. The overall structure of the fixing device in this embodiment is similar to that in the first embodiment. A special part in this embodiment lies in that the mouth-closing device includes a mouth-closing patch 2. The mouth-closing patch 2 is only bonded and fixed to the user's upper and lower lips 11, and does not cover the adjacent region 12 at the periphery of the user's upper and lower lips. This fixing manner is suitable for a user growing a beard or wearing a skincare product in the adjacent region 12 at the periphery of the upper and lower lips. In another embodiment, the mouth-closing patch 2 may also be fixed at the upper and lower lips 11 and the adjacent region 12 at the periphery of the upper and lower lips. The fixing device in this embodiment does not include the strip-shaped patch 7. To ensure a necessary fixing effect, a hole 35 is provided in the connecting piece 3. The hole 35 is located on an outer side of the fixing ring 4. Another closed annular neck strap 36 surrounding the user's head and neck passes through the hole 35. The neck strap 36 can pull the connecting piece 3 from the outer side, to avoid the risk of aspiration of the intraoral apparatus caused when the mouth-closing patch 2 falls off.

Embodiment 5

Figure 17:
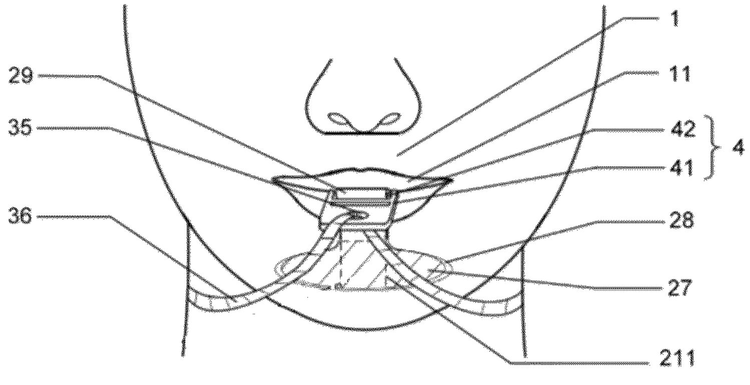
FIG. 17 is a schematic diagram of a structure of a fifth embodiment of a fixing device for fixing an intraoral apparatus being installed on a user's lips according to the present invention.

FIG. 17 shows a fifth embodiment of the present invention. The overall structure of the fixing device in this embodiment is similar to that in the fourth embodiment. A special part in this embodiment lies in that the mouth-closing device includes a mouth patch. The mouth patch does not close the user's mouth. The mouth patch surrounds the fixing ring body 41. An upper end 27 of the mouth patch is fixed to an outer surface of a lower end 28. The lower end 28 is bonded and fixed to a peripheral region of the user's lower lip. In this fixing manner, when the user can open the mouth when wearing the fixing device. The shape of the mouth patch in this embodiment is the same as the shape of the mouth-closing patch 2 in FIG. 8. A bending line 211 is disposed on the upper end 27 of the mouth patch. A bonding layer is not disposed at a middle portion 29. During assembly of the fixing device, the upper end 27 of the mouth patch is bent along the bending line 211 and is inserted from bottom to top in the strip-shaped hole 42 in the third fixing ring 4 arranged at equal intervals in a direction from the outside to the inside of the mouth. Next, the upper end 27 is bent and is inserted from top to bottom in the strip-shaped hole 42 in the second fixing ring 4 arranged at equal intervals in the direction from the outside to the inside of the mouth. In this case, the middle portion 29 surrounds the fixing ring body 41. Next, the upper end 27 is unfolded and bonded to the outer surface of the lower end 28. Finally, the lower end 28 is bonded to the peripheral region of the user's lower lip. The overall structure in another specific embodiment is approximately the same as that in this embodiment. A specific part lies in that a front end 27 of the mouth patch may pass through the strip-shaped hole 42 in the fixing ring 4 on the outermost side, is then wound around the fixing ring body 41 from the outer side of the fixing ring 4, and is then fixed on the outer surface of the lower end 28. The overall structure in another specific embodiment is approximately the same as that in this embodiment. A specific part lies in that the mouth patch may be fixed at another position of the lips, and the mouth patch may be connected to a strip-shaped patch.

Embodiment 6

FIG. 16 may also be used as a schematic diagram of a sixth embodiment of the present invention. The overall structure of the mouth-closing device in this embodiment is similar to that of the fixing device in the fourth embodiment. A special part in this embodiment lies in the following two aspects. First, the mouth-closing device in this embodiment is used to close the user's mouth rather than fixing the intraoral apparatus. Therefore, the connecting mechanism of the fixing device is located on the outer side of the mouth and is not connected to the intraoral apparatus. The connecting mechanism and the neck strap 36 form an aspiration prevention device used to fix the mouth-closing patch 2, to avoid the risk of suffocation due to aspiration of the mouth-closing patch when the mouth-closing patch falls off. The connecting mechanism includes the connecting piece 3 and the fixing ring 42. One end of the connecting piece 3 is connected to the fixing ring 42, and the other end of the connecting piece 3 is connected to the neck strap 36 through the hole 35 provided in the connecting piece. The neck strap 36 pulls the connecting piece 3 from the outer side, to avoid the risk of aspiration caused when the mouth-closing patch 2 falls off. Second, the connecting mechanism in this embodiment is not connected to the intraoral apparatus, and therefore no longer requires a position adjustment function. Therefore, the connecting mechanism includes only one fixing ring, that is, the fixing ring 42 in FIG. 16. Another fixing ring (for example, the fixing ring 41) no longer needs to be disposed. The fixing ring 42 is used to fix the mouth-closing patch 2.

Finally, it should be noted that the foregoing embodiments are merely intended for describing the technical solutions of the present invention rather than limiting the present invention. Although the present invention is described in detail with reference to the embodiments, persons of ordinary skill in the art should understand that they may still make modifications or equivalent replacements to the technical features of the present invention without departing from the spirit and scope of the technical solutions of the technical solutions of the present invention. These modifications or equivalent replacements shall all fall within the scope of the claims the present invention.

The invention claimed is:

1. A fixing device for fixing an intraoral apparatus, comprising a mouth patch, the mouth patch being fixed to an outer side of a user's mouth, wherein the fixing device further comprises a connecting mechanism;

the connecting mechanism connects the mouth patch and the intraoral apparatus;

the connecting mechanism comprises a connecting piece and one or more fixing rings connected to the connecting piece; and the connecting piece is connected to the intraoral apparatus, and the mouth patch passes through the fixing ring, wherein the connecting piece has a sheet structure, and the connecting piece comprises an extraoral end and an intraoral end, and a pair of surfaces formed by the connecting piece configured to join to the user's upper and lower lips are the largest surfaces of the connecting piece.

2. The fixing device according to claim 1, wherein the mouth patch is a mouth-closing patch, an upper portion of the mouth-closing patch is fixed to an upper lip or/and a peripheral region of the upper lip, and a lower portion of the mouth-closing patch is fixed to a lower lip or/and a peripheral region of the lower lip, to maintain a user's mouth in a closed state.

3. The fixing device according to claim 1, wherein the mouth patch has a stacked multilayer structure, and comprises a substrate, a bonding layer, and a covering film; and the bonding layer is disposed on the substrate, and the covering film covers the bonding layer.

4. The fixing device according to claim 1, wherein the mouth patch comprises an upper end, a middle portion, and a lower end, the upper end and the lower end are wider than the middle portion, a bending line is disposed on the upper end or/and the lower end, and the middle portion is tightly engaged with the fixing ring.

5. The fixing device according to claim 1, wherein one end of the mouth patch is fixed to the outer side of the user's mouth, and the other end passes through the fixing ring to be fixed to the fixing device.

6. The fixing device according to claim 1, wherein the fixing ring has a strip-shaped structure, and is tightly engaged with the mouth patch, and the fixing ring comprises a fixing ring body and a strip-shaped hole; and the strip-shaped hole is provided in the fixing ring body.

7. The fixing device according to claim 6, wherein the connecting piece is connected to a plurality of fixing rings arranged at equal intervals in a direction of entering and leaving the oral cavity.

8. The fixing device according to claim 1, wherein a hole and a neck strap are provided on the connecting piece.

9. The fixing device according to claim 1, wherein the mouth patch is connected to one or more strip-shaped patches, and the strip-shaped patch is fixed on the user's face.

10. The fixing device according to claim 2, wherein the fixing device further comprises a reinforcing patch; and the reinforcing patch covers an outer side of the fixing ring in which the mouth-closing patch is located, and is bonded to the outer surface of the mouth-closing patch, and the reinforcing patch holds the fixing ring together with the mouth-closing patch.

11. The fixing device according to claim 10, wherein the reinforcing patch is connected to one or more strip-shaped patches, and the strip-shaped patch is fixed on the user's face.

* * * * *